Figure 1:
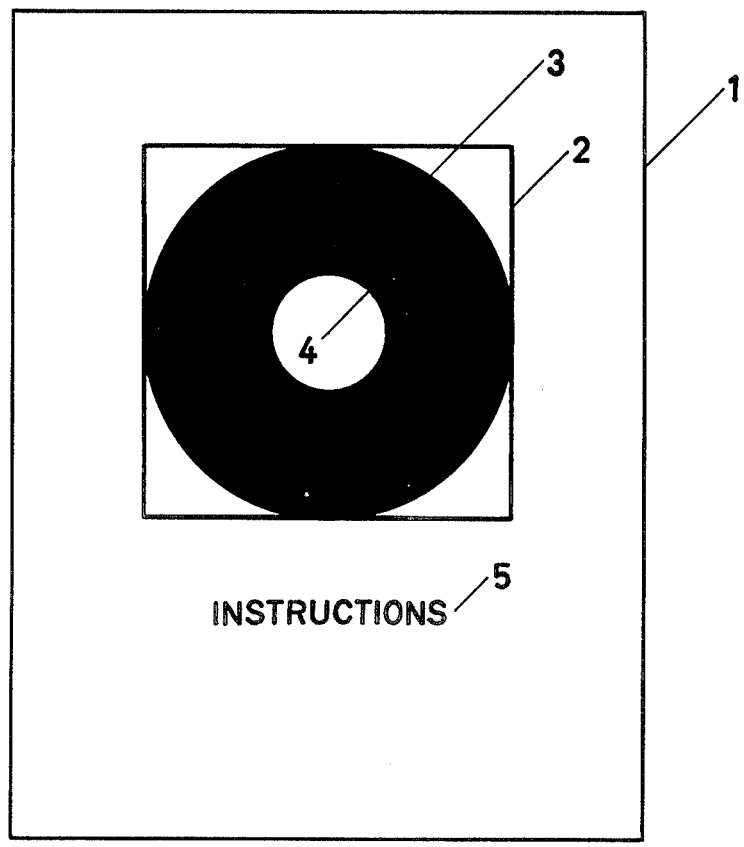

United States Patent [19]

Gogniat

[11] 4,247,201

[45] Jan. 27, 1981

[54] SPECTACLE PRESCRIPT LENS DISTORTION TESTER

[76] Inventor: Nick Gogniat, Rte. 1, Box 211-A, Altoona, Fla. 32702

[21] Appl. No.: 9,265

[22] Filed: Feb. 2, 1979

[51] Int. Cl.³ .......................... G01B 9/00; A61B 3/00
[52] U.S. Cl. ....................................... 356/124; 351/33
[58] Field of Search .......................... 356/124; 351/33

[56] References Cited

U.S. PATENT DOCUMENTS 3,011,394  12/1961  Sherman et al. .................. 351/33

*Primary Examiner*—John K. Corbin
*Assistant Examiner*—Bruce Y. Arnold

[57] ABSTRACT

A visual test target is disclosed which is useful for determining whether a subject's vision is being distorted by previously prescribed spectacle lenses. The target comprises two concentric circles within a square. The larger circle is tangent to each side of the square, and the area between the two circles is imprinted in solid black.

1 Claim, 2 Drawing Figures

U.S. Patent  Jan. 27, 1981  4,247,201

SPECTACLE PRESCRIPT LENS DISTORTION TESTER

This invention relates to ophthalmic instruments and has particular reference to an improved device for testing or determining the correction of prescript spectacle lenses, particularly in reference to possible distortion of objects seen.

Prior art eye test charts, such as the letter eye chart positioned on a wall in front of a subject generally is an adequate test chart for testing the visual acuity of the subject and for prescribing corrective lenses accordingly. In the letter eye chart the subject may see, for example the letter "O" distinctly and clearly at the testing distance while wearing spectacles, however the letter is too small to enable the examiner to know if there was any distortion introduced by the corrective lenses used to obtain this visual acuity. The examiner does not know if the subject sees an "O" as a perfect circle, an egg shape, an ellipse, or other shapes. He only knows it is readable.

As another example, when viewing the capital letter "E", the examiner would not know if the letter "E" appears to the subject to be flattened, elongated, or leaning to the left or right. The examiner knows only that the subject was able to read the letter at the testing distance.

The letter eye chart, when positioned on the wall, appears in a vertical plane and has two dimensions, length and width. However, during the majority of the time, a person's vision uses three dimensions, length, width, and depth. Thus, the letter eye chart does not enable the examiner to determine the effect the prescribed lenses will have when they are used to view three dimensional scenes.

The main object of this invention is to detect distortion which may have been introduced by spectacle lenses and which would not otherwise be detected when testing using the letter eye chart.

Other objects and advantages of the invention will become apparent when the following description is considered in conjunction with the accompanying drawing.

Referring to FIG. 1, the test target consists of numeral 1 which is a dark colored square drawn on a light background, numeral 2 is a dark circle drawn tangent to the sides of the square, numeral 3 is a concentric dark circle whose diameter is conveniently smaller than the numeral 2 circle.

Figure 2:
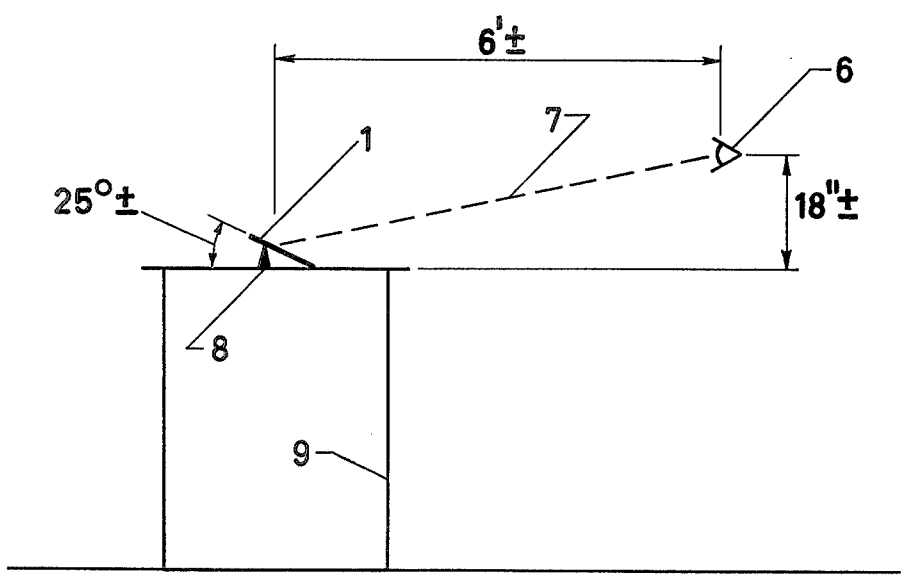

FIG. 2 of the drawing illustrates the test chart 1 in use, supported by a table 9 and stand 8 and positioned about 18 inches below and six feet in front of the eye 6 of an observer so that the line of sight 7 is unobstructed.

The test target may be placed in any convenient position which would be apparent to those of ordinary skill in the art after reading this disclosure. For example if the test target was placed horizontally on a table and the subject was at a convenient distance with his eye level slightly above the test chart, this would enable the subject being tested to identify the shapes he sees, orally or by drawings, as: circles, ellipses, egg shapes, ovals, rectangles, trapezoids, quadrilaterals, or a combination of such shapes.

According to the response of the subject the examiner could make modifications in the lenses to correct any distortion introduced by them and not otherwise detectable by testing with the letter eye chart.

It is apparent that there has been provided by this invention a device by which various objects and advantages hereinbefore set forth are successfully achieved.

Modifications of this invention not described herein will become apparent to those of ordinary skill in the art after reading this disclosure. Therefore it is intended that the matter contained in the foregoing description and the accompanying drawing be interpreted in an illustrative sense, and not in a limiting sense, when consideration is given to the appended claims.

I claim:

1. A test target for detecting distortion introduced by spectacle lenses, said target comprising: two concentric circles within a square wherein the larger circle is tangent to each side of the square, and wherein the area between said concentric circles is imprinted in solid black.

* * * * *